US009801754B2

(12) United States Patent
Masters et al.

(10) Patent No.: US 9,801,754 B2
(45) Date of Patent: Oct. 31, 2017

(54) PARACHUTE OSTOMY POUCH

(75) Inventors: Brock Edward Masters, Des Plaines, IL (US); Robert Anthony Davis, Beach Park, IL (US)

(73) Assignee: HOLLISTER INCORPORATED, Libertyville, IL (US)

( * ) Notice: Subject to any disclaimer, the term of this patent is extended or adjusted under 35 U.S.C. 154(b) by 250 days.

(21) Appl. No.: 14/127,102

(22) PCT Filed: Mar. 1, 2012

(86) PCT No.: PCT/US2012/027215
§ 371 (c)(1),
(2), (4) Date: Jan. 9, 2014

(87) PCT Pub. No.: WO2013/022487
PCT Pub. Date: Feb. 14, 2013

(65) Prior Publication Data
US 2014/0148770 A1    May 29, 2014

Related U.S. Application Data

(60) Provisional application No. 61/521,599, filed on Aug. 9, 2011.

(51) Int. Cl.
*A61F 5/445* (2006.01)
*A61F 5/44* (2006.01)

(52) U.S. Cl.
CPC ............ *A61F 5/4404* (2013.01); *A61F 5/445* (2013.01); *A61F 5/4407* (2013.01)

(58) Field of Classification Search
USPC ................................................ 604/344, 332
See application file for complete search history.

(56) References Cited

U.S. PATENT DOCUMENTS

| 4,296,749 | A | | 10/1981 | Pontifex |
| 5,248,308 | A | | 9/1993 | von Emster |
| 5,865,819 | A | * | 2/1999 | Cisko, Jr. ............... A61F 5/445 604/327 |
| 7,604,622 | B2 | | 10/2009 | Pedersen et al. |
| 7,704,240 | B2 | | 4/2010 | Buhl |
| 7,815,618 | B2 | * | 10/2010 | Schena ................ A61F 5/4407 604/332 |
| 2004/0059306 | A1 | * | 3/2004 | Tsal ..................... A61F 5/4404 604/332 |

(Continued)

FOREIGN PATENT DOCUMENTS

JP   2004528949 A   9/2004
WO   2005082271 A2  9/2005

(Continued)

OTHER PUBLICATIONS

Supplemental European Search Report for EP 12821419 dated Feb. 23, 2015.

(Continued)

*Primary Examiner* — Todd J Scherbel
*Assistant Examiner* — Guy K Townsend
(74) *Attorney, Agent, or Firm* — Levenfeld Pearlstein, LLC

(57) ABSTRACT

An ostomy appliance is sufficiently small to provide the user with a desired level of discretion, and can also provide an expanded collection capacity to accommodate sudden outflows of stomal discharge.

15 Claims, 3 Drawing Sheets

(56) References Cited

U.S. PATENT DOCUMENTS

| | | | |
|---|---|---|---|
| 2004/0171999 A1* | 9/2004 | Andersen | A61F 5/4407 604/332 |
| 2005/0159717 A1 | 7/2005 | Holtermann | |
| 2005/0283126 A1 | 12/2005 | Schena et al. | |
| 2007/0260206 A1* | 11/2007 | Mullejans | A61F 5/445 604/332 |
| 2008/0004580 A1* | 1/2008 | Mullejans | A61F 5/441 604/344 |
| 2008/0097360 A1* | 4/2008 | Andersen | A61F 5/4407 604/332 |
| 2008/0269698 A1 | 10/2008 | Alexander et al. | |
| 2014/0148770 A1* | 5/2014 | Masters | A61F 5/4407 604/344 |

FOREIGN PATENT DOCUMENTS

| | | |
|---|---|---|
| WO | 2005082272 A2 | 9/2005 |
| WO | 2010030426 A1 | 3/2010 |
| WO | 20111031822 A1 | 3/2011 |

OTHER PUBLICATIONS

International Preliminary Report on Patentability for PCT/US2012/027215 dated Feb. 20, 2014.

* cited by examiner

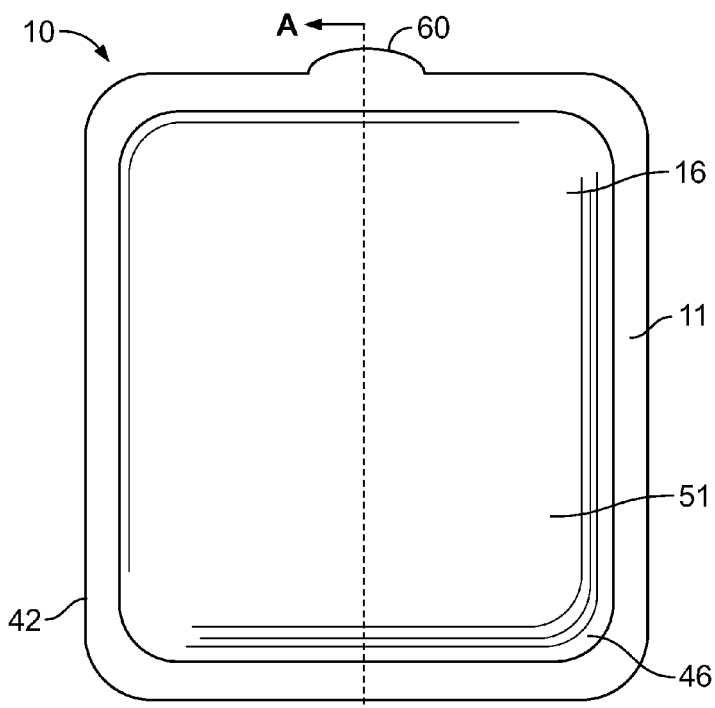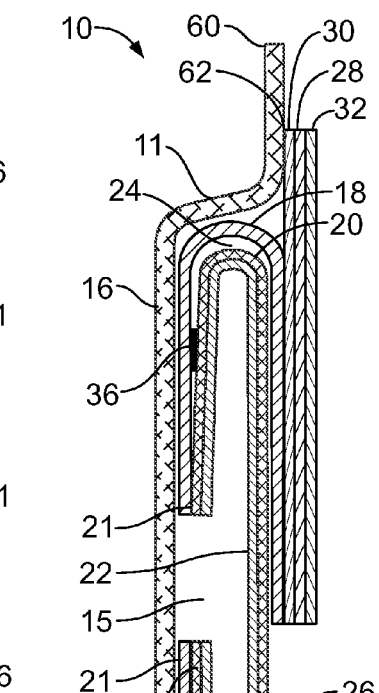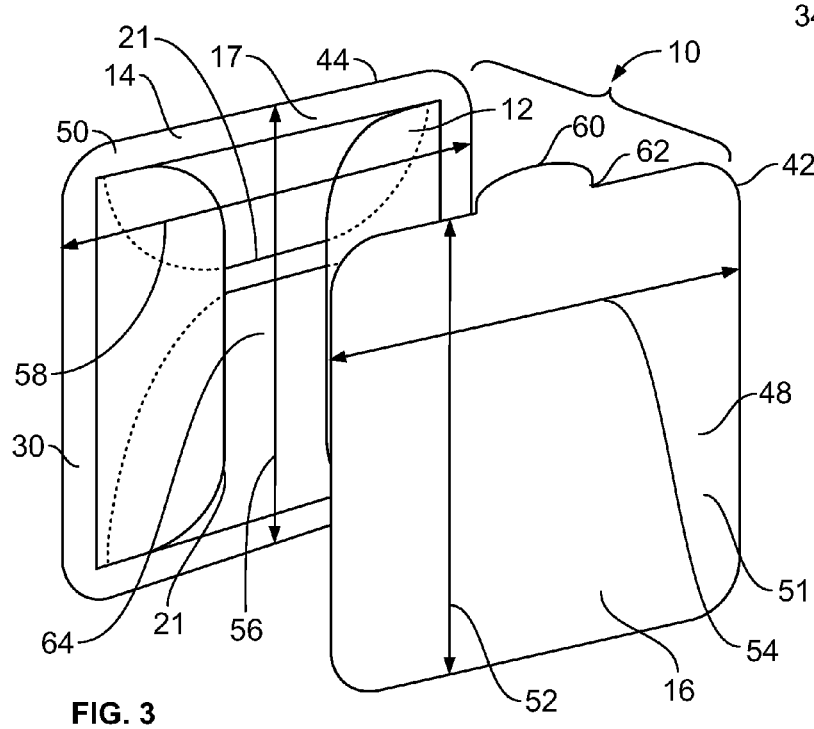

PARACHUTE OSTOMY POUCH

CROSS-REFERENCE TO RELATED APPLICATIONS

This is a National Stage Application of International Patent Application No. PCT/US012/027215, filed Mar. 1, 2012, which claims the benefit of and priority to US Provisional Application No. 61/521,599, filed Aug. 9, 2011, the contents of which are incorporated fully by reference herein.

BACKGROUND

The present disclosure relates to ostomy appliances, and more particularly to an ostomy pouch for collecting body waste through a stomal opening for later disposal.

Ostomy pouches for the collection of body waste are well known. Ostomy pouches typically include flat, opposing side walls secured together along their edges to define a collection cavity. One of the side walls is provided with an opening to receive a stoma, and means such as a connecting flange is provided for securing the pouch to an adhesive barrier placed to surround the stoma so that body waste discharged through the stoma is received within the cavity. At its lower end, the ostomy pouch may have a discharge opening which may be closed during collection of the body waste material but may be opened for draining the body waste material from the pouch after a period of use. Alternatively, the ostomy pouch may be designed for a single use, in which case, it will not be provided with a discharge opening since the entire pouch will be discarded after it has substantially filled with stomal discharge.

Ostomy pouches are available in various sizes for different collecting capacity needs for different users or for different situations of an individual user. For example, the user will want to use a large ostomy bag over night, but may desire to use a smaller ostomy bag or cap for discretion during public activities or when exercising. However, as stomal discharge cannot be regulated at will, the small ostomy bag or cap may not provide sufficient collection capacity to contain a sudden outflow of stomal discharge.

Accordingly, there is a need for an improved ostomy pouch that is small enough to provide the discretion desired by the user, yet can also provide a sufficient collection capacity to contain sudden outflows of stomal discharge.

BRIEF SUMMARY

A mini ostomy pouch according to various embodiments is sufficiently small to provide a higher degree of discretion for the user, yet configured to expand to provide collection capacity of a full size ostomy pouch to accommodate sudden outflows of stomal discharge, thereby providing the user with added security.

In one aspect, an ostomy appliance includes a pouch and a tear-away panel. The pouch includes an inlet and two walls, to wit, a body side wall and an outer wall, which are sealed together along their peripheral edges to define a cavity for collecting body waste. The ostomy appliance has a compacted state and a deployed state. The ostomy appliance in the deployed state has a surface area, which is greater than that of the ostomy appliance in the compacted state. The ostomy appliance is configured to change from the compacted state to the deployed state by removing the tear-away panel.

In another aspect, an ostomy appliance includes a pouch and a tear-away panel. The pouch includes an inlet and two walls, to wit, a body side wall and an outer wall, which are sealed together along their peripheral edges to define a cavity for collecting body waste. The ostomy appliance has a compacted state and a deployed state. In the compacted state, the peripheral edges of the pouch walls are hidden behind the tear-away panel.

Any of above described ostomy appliances can further include a skin barrier arranged about the inlet. The skin barrier includes a barrier backing and an adhesive for attaching the ostomy appliance on a user, such that the body waste flows into the cavity through the inlet. The barrier backing is laminated on the pouch side surface of the adhesive. The body side wall of the pouch is attached to the barrier backing proximate the inlet, and the tear-away panel is attached along peripheral edges of the barrier backing. The pouch is folded or gathered such that the pouch is contained between the barrier backing and the tear-away panel in the compacted state.

Any of above described ostomy appliances can further include a pull-tab arranged proximate a peripheral edge of the tear-away panel. The pull-tab may be integrally formed with the tear-away panel or may be a separate piece arranged between the tear-away panel and the barrier backing. The tear-away panel can be peelably attached to the barrier backing such that the tear-away panel is peeled away from the barrier backing by pulling on the pull-tab. In one embodiment, the tear-away panel is peelably attached to the barrier backing by heat sealing. In another embodiment, the tear-away panel is peelably attached to the barrier baking by an adhesive.

In some embodiments, the ostomy appliance can include a two-piece ostomy pouch including a pouch side coupling ring and a body side coupling ring, wherein the pouch is folded or gathered behind the tear-away panel when in the compacted state.

Any of the above described ostomy appliances can include the tear-away panel formed of a non-woven sheet.

Any of the above described ostomy appliances has a first body waste collection capacity when in the compacted state and a second body waste collection capacity when in the deployed state, wherein the second body waste collection capacity is greater than the first body waste collection capacity. In one embodiment, the second body waste collection capacity is at least three times greater than the first body waste collection capacity.

Any of the above described ostomy appliances can include a single use disposable pouch without an outlet, or a pouch including an outlet with a closure mechanism.

Other aspects, objectives and advantages will become more apparent from the following detailed description when taken in conjunction with the accompanying drawings.

BRIEF DESCRIPTION OF THE SEVERAL VIEWS OF THE DRAWINGS

The benefits and advantages of the present embodiments will become more readily apparent to those of ordinary skill in the relevant art after reviewing the following detailed description and accompanying drawings, wherein:

FIG. 1 is a perspective view of an ostomy appliance including a one-piece ostomy pouch in a compacted state according to an embodiment;

FIG. 2 is an exploded view of the ostomy appliance of FIG. 1;

FIG. 3 is a cross-sectional view of the ostomy appliance of FIG. 1 taken along line A-A;

DETAILED DESCRIPTION

Figure 4:
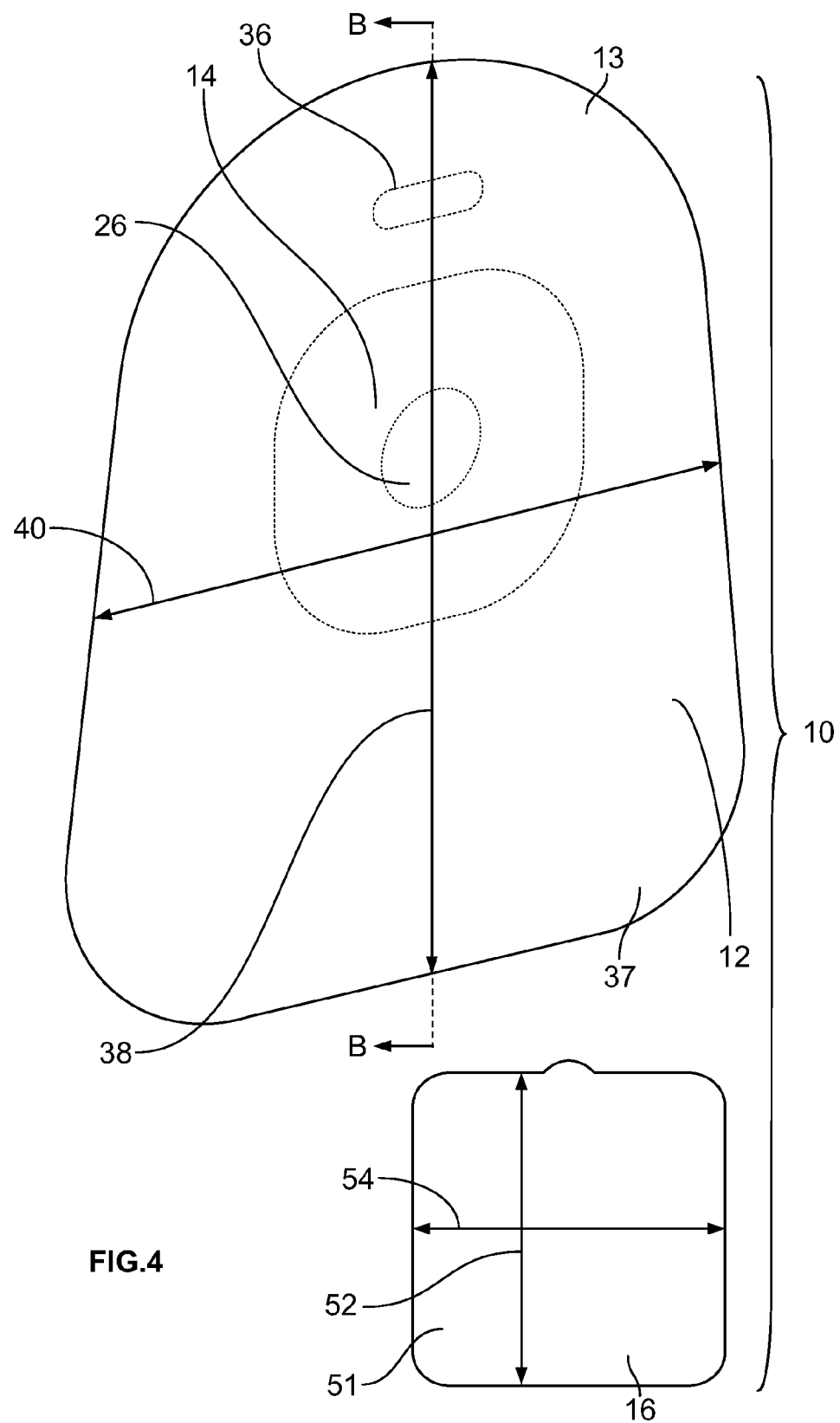
FIG. 4 is a perspective view of the ostomy appliance of FIG. 1 in a deployed state.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

Referring now to the figures, FIGS. 1-4 show an embodiment of an ostomy appliance 10. FIGS. 1 and 2 illustrate the ostomy appliance 10 in a compacted state 11, and FIG. 4 illustrates the ostomy appliance 10 in a deployed state 13. The ostomy appliance 10 generally includes a pouch 12, a skin barrier 14, and a tear-away panel 16. As shown in FIG. 4, the pouch 12 is a full size ostomy pouch, which can be provided in different sizes.

As shown in an exploded view in FIG. 3 and a cross-sectional view in FIG. 2, the pouch 12 is folded and secured in place with the tear-away panel 16, such that the pouch 12 is completely contained within a cavity 15 defined between the tear-away panel 16 and the skin barrier 14. The tear-away panel 16 is peelably attached to the pouch side surface 17 of the skin barrier 14 to form the ostomy appliance 10 in the compacted state 11, as shown in FIGS. 1 and 2. The ostomy appliance 10 in the compacted state 11 is significantly smaller in size when compared to the ostomy appliance 10 in the deployed state 13 (FIG. 4), in which the pouch 12 is fully deployed.

The ostomy appliance 10 in the compacted state 11 is also referred to herein as a mini pouch or a mini ostomy appliance due to the significant reduction in size when compared to the fully deployed, full size ostomy pouch. The mini pouch in the illustrated embodiment has substantially the same surface area as the peel-away panel. The mini pouch can come in many different sizes, preferably in a size similar to ostomy caps. When a large capacity pouch is needed, the user can remove the tear-away panel 16 to deploy the pouch 12. Thus, the user can wear the mini pouch when more discretion is desired, such as in public, without concern about conditions due to leakage caused by, for example, a sudden outflow of stoma discharge.

Figure 5:
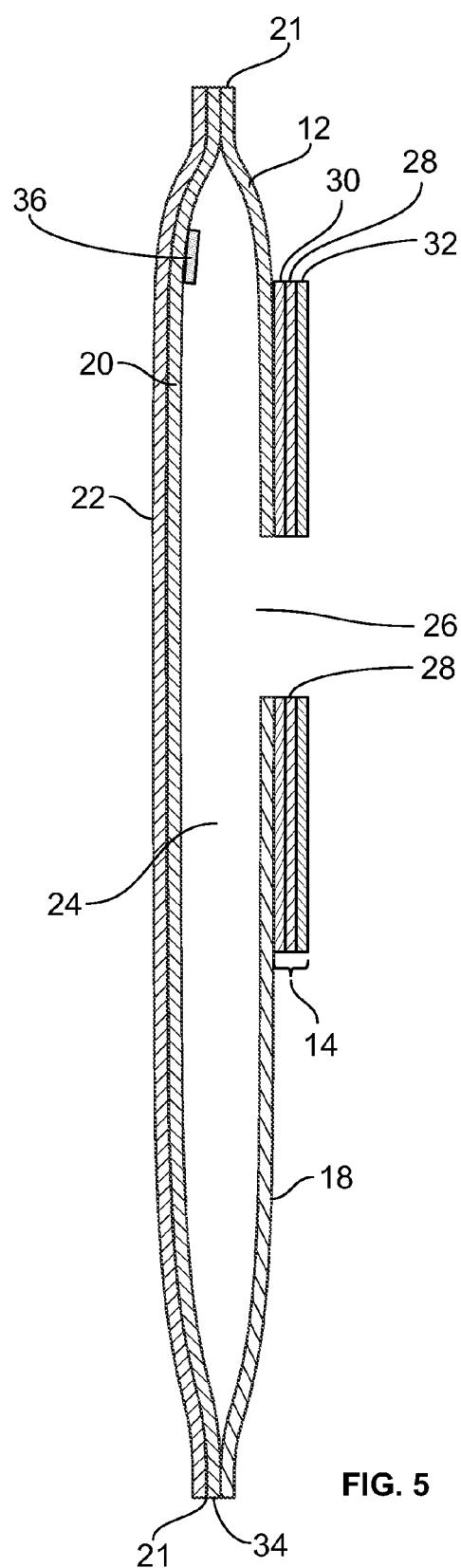
FIG. 5 is a cross-sectional view of the one-piece ostomy pouch of FIG. 4 taken along line B-B.

With the ostomy appliance 10, generally described, additional structural details of the ostomy appliance 10 will be described. As shown FIGS. 2 and 5, the pouch 12 includes a body side wall 18, an outer wall 20, and a non-woven sheet 22. The body side wall 18 and the outer wall 20 are sealed together along their outer peripheral edges 21 to define a cavity 24 for collecting stoma discharge. The non-woven sheet 22 is attached on the outer surface of the outer wall 20. The non-woven sheet is optional, thus some embodiments may not include the non-woven sheet or may include the non-woven sheet only on the outer surface of the body side wall or on the outer surfaces of both walls.

The pouch 12 of this embodiment is designed for a single use, thus has a closed end 34 without a discharge outlet. In other embodiments, the pouch may include a discharge outlet which may be closed during collection of the stoma discharge and opened for periodic draining of the stoma discharge from the pouch. For example, the pouch may include an outlet with a fold-up type closure, such as those disclosed in Villefrance, et al., U.S. Pat. No. 7,879,015, and Mandzij, et al., U.S. Pat. No. 7,879,016, both of which are commonly assigned with the present application and are incorporated herein by reference. In such embodiments, the discharge opening is closed before the pouch is folded and secured with the tear-away panel to form the mini ostomy appliance.

The body side wall 18 is provided with an inlet opening 26 to receive a stoma. The skin barrier 14 is arranged about the inlet opening 26 for attachment around the stoma. The skin barrier 14 includes an adhesive 28, a barrier backing 30, and a release liner 32. The barrier backing 30 is laminated on the pouch side surface of the adhesive 28. The body side wall 18 is attached to the barrier backing 30 proximate the inlet opening 26. The body side wall 18 can be attached to the barrier backing 30 via any suitable methods, such as an adhesive or heat sealing. Preferably, the body side wall 18 is heat sealed to the barrier backing 30. The body side wall 18 and the outer wall 20 can be formed of the same material or different materials, which can be a single layer film or a multilayer film. The barrier backing 30 may also be formed of a single layer film or a multilayer film. Preferably, the body side wall 18 and the barrier backing 30 are formed of films, which include a heat sealable surface layer, such that the body side wall 18 and the barrier backing 30 can be heat sealed together.

The pouch 12 may also be provided with a filter 36, such as those disclosed in Nolan, U.S. Pat. No. 3,952,727, and Botten, U.S. Pat. No. 7,559,922, both of which are commonly assigned with the present application and are incorporated herein by reference. The filter 36 is strategically arranged on the pouch 12 such that flatus gases in the pouch 12 can still exit via the filter 36 when the ostomy appliance 10 is in the compacted state 11. Although, the filter 36 of the illustrated embodiment is attached to an inner surface of the pouch 12, in other embodiments, the filter may be attached on an outer surface of the pouch, or the pouch may not include a filter.

The tear-away panel 16 is shaped and sized such that an outer periphery 42 of the tear-away panel 16 generally matches an outer periphery 44 of the skin barrier 14, as shown in FIGS. 2 and 3. The tear-away panel 16 includes a pull-tab 60 extending from a peripheral edge 62. The pull-tab 60 is integrally formed with the tear-away panel 16 in this embodiment, however, the pull-tab may be a separate member arranged between the tear-away panel 16 and the barrier backing 30 in other embodiments, such that the pull-tab extends out of the sealed peripheral edges of the tear-away panel and the barrier backing Although the pull-tab 60 is arranged on the top peripheral edge 62 of the tear-away panel 16 in the illustrated embodiment, the pull-tab can be arranged in different peripheral locations, such as at a corner or on a bottom peripheral edge, as long as the user can grasp the pull-tab and apply a pulling force to remove or peel away the tear-away panel 16 from the barrier backing 30.

To form the ostomy appliance 10 in a compacted state 11, the pouch 12 is folded or gathered toward a center 64 on the barrier backing 30, such that the peripheral edges 21 of the pouch 12 do not extend beyond the outer periphery 44 of the skin barrier. The pouch 12 is folded or gathered to leave a sealing space 50 proximate the outer periphery 44 of the skin barrier 14 for the attachment of the tear-away panel 16. When folding or gathering the pouch 12, the folds or gathers are formed such that the filter 36 is not obstructed by the folds or gathers to allow flatus gasses in the pouch 12 to exit the ostomy appliance 10 via the filter 36 and through the tear-away panel 16 when in the compacted state 11.

The tear-away panel 16 is peelably attached to the barrier backing 30 such that the tear-away panel 16 can be removed or peeled away from the barrier backing 30 without ripping or damaging the skin barrier 14. Further, the peelable attachment between the tear-away panel 16 and the barrier backing 30 is configured such that the tear-away panel 16 can be easily removed from the barrier backing 30 without interrupting a seal between the adhesive 28 and user's skin. Such peelable attachment between the tear-away-panel 16 and the barrier backing 30 can be obtained via any suitable method, such as peelable adhesives or heat sealing. The tear-away panel 16 can be formed of any suitable material, such as a polymeric film or a non-woven sheet, preferably, a non-woven sheet. Preferably, the tear-away panel 16 is formed of a material, which can form a peelably seal with the barrier backing 30 by heat sealing.

In the illustrated embodiment, the pouch 12 is folded in four ways, such that the peripheral edges 21 of the pouch 12 are folded toward the center of the barrier backing 30 to form the ostomy appliance 10 in the compacted state 11. In other embodiments, the pouch 12 can be folded less than four times or greater than four times as long as the pouch 12 is contained within the cavity 15 formed between the barrier backing 30 and the tear-away panel 16 when their peripheries 42, 44 are sealed together. For example, the pouch 12 can be gathered on the barrier backing 30 with multiple gathers to fit between the barrier backing 30 and the tear-away panel 16.

The pouch 12 can come in various sizes. In one embodiment, the pouch 12 has a surface area 37 with a length 38 of about 9 inches and a width 40 of about 6 inches when fully deployed, as shown in FIG. 4. The tear-away panel 16 has a generally a rectangular shape with rounded corners, and has a surface area 51 with a length 52 of about 4 inches and a width 54 of about 4 inches. The skin barrier 14 has a corresponding shape and sizes such that the outer peripheries of the tear-away panel 16 and the skin barrier 14 generally match when sealed together to form the mini pouch. The pouch 12 is folded or gathered, and secured in place by attaching the tear-away panel 16 on the peripheral edges of the barrier backing 30 to form the ostomy appliance 10 in the compacted state 11. As such, the ostomy appliance 10 in the compacted state 11 has a surface area 51 equal to that of the tear-away panel 16. The appliance 10 in the deployed state 13 has a surface area 37, which is the same as that of the fully deployed pouch 12. The mini pouch can come in various shapes and sizes. For example, the mini pouch can have a circular shape with a diameter of about 3 inches.

When in use, the user attaches the ostomy appliance 10 in the compacted state 11 around the stoma by peeling off the release liner 32 and placing the exposed adhesive around the stoma, such that the stoma is received in the inlet opening 26 to allow stoma discharge to flow into the cavity 24. The ostomy appliance 10 in the compacted state 11 provides the user with a higher degree of discretion with a significant reduction in the ostomy appliance size when compared to the fully deployed pouch 12 in the deployed state 13. However, since the pouch 12 is folded or gathered, and contained within the cavity 15 between the tear-away panel 16 and the barrier backing 30, a collection capacity of the pouch 12 is also significantly reduced as the pouch can only expand within the cavity 15 to hold the stoma discharge. Although, the collection capacity is smaller when compared to the fully deployed pouch 12, the mini pouch can still contain some stomal discharge and allow flatus gasses to exit via the filter 36, while the user enjoys the higher degree of discretion. When the user desires to increase the collection capacity, for example to accommodate sudden outflows of stomal discharge, the user can pull on the pull-tab 60 to remove the tear-away panel 16 to deploy the pouch 12. In the deployed state 13, the fully deployed pouch 12 provides the user with an increased collection capacity to contain the stomal discharge without leakage. In one embodiment, the collection capacity of the ostomy appliance in the deployed state is greater than that of the ostomy appliance in the compacted state by at least 2 times, and preferably by at least 3 times. Thus, the ostomy appliance 10 provides the user with a desirable mini pouch with the capability to increase the collection capacity.

Figure 6:
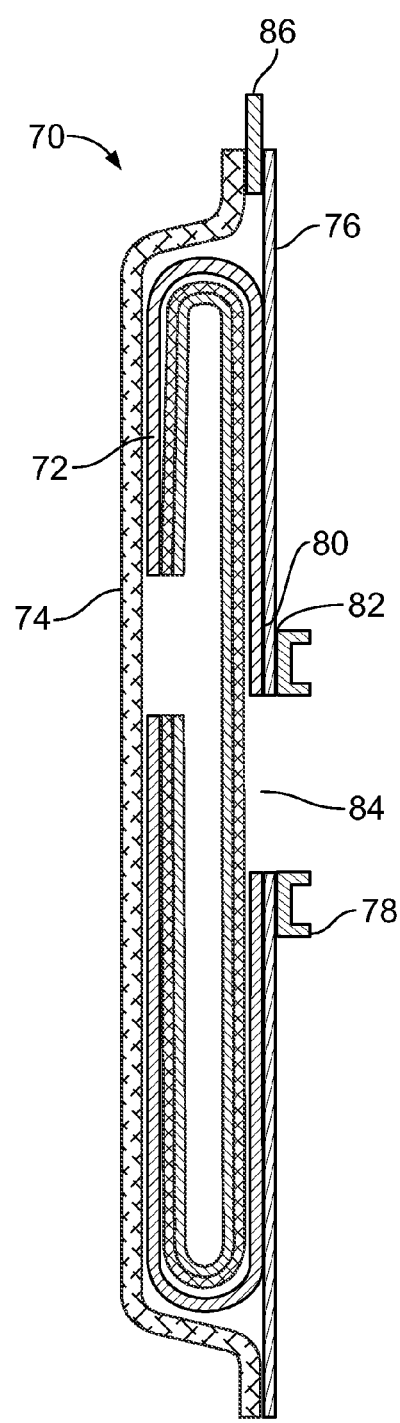
FIG. 6 is a cross-sectional view of an ostomy appliance including a two-piece ostomy pouch according to another embodiment.

FIG. 6 shows a cross-sectional view of a mini pouch 70 according another embodiment. Similar to the ostomy appliance 10, the mini pouch 70 includes a pouch 72 and a tear-away panel 74. However, the pouch 72 is a two-piece pouch with a pouch side coupling ring 78, instead of the skin barrier 14 of the ostomy appliance 10. The pouch side coupling ring 78 is configured to mate with a body side coupling ring (not shown) on a skin barrier (not shown). In this embodiment, the skin barrier is first attached to the user around a stoma, and the mini pouch 70 is attached to the skin barrier by coupling the pouch side coupling ring 78 with the body side coupling ring (not shown.)

The mini pouch 70 also includes a backing panel 76. The pouch 72 is attached on a first surface 80 of the backing panel 76 about an inlet opening 84, and the pouch side coupling 78 is attached on a second surface 82 of the backing panel 76. Other aspects of the pouch 72 are the same as pouch 12 of the previously described embodiment. The mini pouch 70 includes a pull-tab 86, which is arranged between the tear-away panel 74 and the backing panel 76 proximate their peripheral edges. The pull-tab 86 is attached at least to the tear-away panel 74 or attached both to the tear-away panel 74 and the backing panel 76. Preferably, the pull-tab 86 is permanently attached to the tear-away panel 74, such that the pull-tab 86 remains attached to the tear-away panel 74 as the user pulls on the pull-tab to remove the tear-away panel 74 to deploy the pouch 72. As it was with the ostomy appliance 10, the mini pouch 70 is formed by folding and gathering the pouch 72. The folded or gathered pouch 72 is secured in place by sealing the peripheral edges of the tear-away panel 74 and the backing panel 76 together. The collection capacity of the mini pouch 70 can be increased by removing the tear-away panel 74 and deploying the pouch 72, as described in detail above with regard to the ostomy appliance 10.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. An ostomy appliance, comprising:
   a pouch, the pouch being the only pouch of the ostomy appliance and including an inlet, a body side wall, and an outer wall, wherein the body side wall and the outer wall are sealed together along their peripheral edges to define a cavity for collecting body waste;
   a tear-away panel; and
   a skin barrier arranged about the inlet, the skin barrier including a barrier backing and an adhesive for attaching the ostomy appliance on a user such that the body waste flows into the cavity through the inlet, the barrier backing being laminated on a pouch side surface of the adhesive, wherein the body side wall is attached to the barrier backing proximate the inlet, and the tear-away panel is attached along outer peripheral edges of the barrier backing, wherein peripheral edges of the pouch are folded or gathered such that a bottom portion of the pouch is arranged adjacent an outer surface of the pouch and the pouch including the entire outer peripheral edges is contained between the barrier backing and the tear-away panel in the compacted state, wherein the ostomy appliance has a compacted state having a first surface area, and a deployed state having a second surface area, the second surface area being greater than the first surface area, and wherein the ostomy appliance is configured to change from the compacted state to the deployed state by removing the tear-away panel,
   wherein the ostomy appliance in the compacted state is configured to collect body waste and has a first body waste collection capacity, and the ostomy appliance in the deployed state is configured to collect body waste and has a second body waste collection capacity, wherein the second body waste collection capacity is greater than the first body waste collection capacity.

2. The ostomy appliance of claim 1, further including a pull-tab arranged proximate a peripheral edge of the tear-away panel, wherein the tear-away panel is peelably attached to the barrier backing such that the tear-away panel is peeled away from the barrier backing by pulling on the pull-tab.

3. The ostomy appliance of claim 2, wherein the tear-away panel is peelably attached to the barrier backing by heat sealing.

4. The ostomy appliance of claim 2, wherein the tear-away panel is peelably attached to the barrier baking by an adhesive.

5. The ostomy appliance of claim 1, wherein the tear-away panel comprises a non-woven sheet.

6. The ostomy appliance of claim 1, wherein the pouch is a single use disposable pouch without an outlet.

7. The ostomy appliance of claim 1, wherein the pouch includes an outlet with a closure mechanism.

8. An ostomy appliance, comprising:
   a pouch, the pouch being the only pouch of the ostomy appliance and having an inlet, a body side wall, and an outer wall, wherein the body side wall and the outer wall are sealed together along their peripheral edges to define a cavity for collecting body waste;
   a tear-away panel; and
   wherein the ostomy appliance has a compacted state and a deployed state, wherein the pouch walls including the entire outer peripheral edges are contained and hidden behind the tear-away panel in the compacted state, wherein a bottom portion of the pouch is arranged adjacent an outer surface of the pouch in the compacted state, and wherein the ostomy appliance is configured to change from the compacted state to the deployed state by peeling away the tear-away panel from the ostomy appliance,
   wherein the ostomy appliance in the compacted state is configured to collect body waste and has a first body waste collection capacity, and the ostomy appliance in the deployed state is configured to collect body waste and has a second body waste collection capacity, wherein the second body waste collection capacity is greater than the first body waste collection capacity.

9. The ostomy appliance of claim 8, wherein the pouch is a one-piece pouch including a skin barrier arranged about the inlet, the skin barrier including a barrier backing and an adhesive for attaching the ostomy appliance on a user such that the body waste flows into the cavity through the inlet, the barrier backing being laminated on a pouch side surface of the adhesive, wherein the body side wall is attached to the barrier backing proximate the inlet, and wherein the tear-away panel is attached along peripheral edges of the barrier backing.

10. The ostomy appliance of claim 9, wherein the pouch has a larger surface area than the tear-away panel, and the pouch is folded or gathered such that the pouch is covered by the tear-away panel without any portion of the pouch extending beyond the peripheral edges of the tear-away panel.

11. The ostomy appliance of claim 10, further including a pull-tab arranged proximate a peripheral edge of the tear-away panel, wherein the tear-away panel is peelably attached to the barrier backing such that the tear-away panel is peeled away from the barrier backing by pulling on the pull-tab.

12. The ostomy appliance of claim 8, wherein the tear-away panel is removed from the ostomy appliance when in the deployed state, wherein the pouch is fully deployed to provide a maximum body waste collection capacity in the deployed state.

13. The ostomy appliance of claim 8, wherein the ostomy pouch is a two-piece ostomy pouch including a pouch side coupling ring and a body side coupling ring, wherein the pouch is folded or gathered behind the tear-away panel when in the compacted state.

14. The ostomy appliance of claim 8, wherein the tear-away panel comprises a non-woven sheet.

15. The ostomy appliance of claim 8, wherein the ostomy appliance has a first body waste collection capacity when in the compacted state and a second body waste collection capacity when in the deployed state, wherein the second body waste collection capacity is at least three times greater than the first body waste collection capacity.

* * * * *